United States Patent [19]

Martin et al.

[11] Patent Number: 4,585,453
[45] Date of Patent: Apr. 29, 1986

[54] DISPOSABLE HOLDER FOR PROSTHETIC HEART VALVE

[75] Inventors: Richard L. Martin, Fountain Valley; Michael B. Baranowski, Corona Del Mar, both of Calif.

[73] Assignee: Shiley, Incorporated, Irvine, Calif.

[21] Appl. No.: 468,561

[22] Filed: Feb. 22, 1983

[51] Int. Cl.⁴ .................. A61F 2/24; A61B 17/00
[52] U.S. Cl. .................... 623/2; 128/303 R
[58] Field of Search ............ 3/1.5; 128/303 R, 303 A, 128/334 R, 321, 354; 623/2

[56] References Cited

U.S. PATENT DOCUMENTS

| | | | |
|---|---|---|---|
| 2,082,062 | 6/1937 | Johnson | 128/354 |
| 2,406,393 | 8/1946 | Neugass | 128/354 |
| 3,409,013 | 11/1968 | Berry | 3/1.5 X |
| 3,587,115 | 6/1971 | Shiley | 623/2 |
| 3,628,535 | 12/1971 | Ostrowsky et al. | 128/303 R |
| 3,828,787 | 8/1974 | Anderson et al. | 128/303 R |
| 3,860,005 | 1/1975 | Anderson et al. | 128/303 R |
| 4,057,857 | 11/1977 | Fettel | 3/1.5 |
| 4,065,816 | 1/1978 | Sawyer | 128/303 R X |
| 4,182,446 | 1/1980 | Penny | 623/2 X |
| 4,185,636 | 1/1980 | Gabbay et al. | 128/303 R X |
| 4,211,325 | 7/1980 | Wright | 623/2 X |

OTHER PUBLICATIONS

"A Suture Holder and Separator Attachment to the Starr-Edwards Prosthetic Valve Holders" by J. T. Grismer et al, Surgery, Gynecology & Obstetrics, Mar. 1965, pp. 583-584.

Primary Examiner—Ronald L. Frinks
Attorney, Agent, or Firm—Knobbe, Martens, Olson & Bear

[57] ABSTRACT

A disposable heart valve holder is correctly prepositioned on a prosthetic heart valve and is provided with a pair of resilient fingers in snapping engagement with the interior surface of an annular prosthesis. Each finger of the holder is provided with a detent for retention of the heart valve ring and with a grip for manual manipulation of the holder. The holder is rotatably removed or reattached to the heart valve in order to reduce trauma to the patient and decrease the time required for replacement surgery. One of the fingers of the holder is relatively more flexible than the other and is provided with a tapered leading edge in order to facilitate the removal or reattachment of the holder.

20 Claims, 2 Drawing Figures

DISPOSABLE HOLDER FOR PROSTHETIC HEART VALVE

BACKGROUND OF THE INVENTION

A common surgical technique currently available is the complete replacement of a malfunctioning or damaged human heart valve with a prosthetic valve. While the mortality rate for such replacement has improved considerably over the last few years, certain dangers still exist. For example, there is a recognized incidence of failure of these operations due to the trauma occasioned by the replacement operation itself. For most prosthetic heart valves, the suturing of the valve in place requires an extended period of time during which extra-corporeal perfusion and coronary-pulmonary bypass is necessary.

Typically, the prosthetic heart valve is provided with a suture ring, generally made from a cloth material or some other biologically compatible material, which is used in suturing the heart valve in position within the heart. The valve is secured by sutures connecting the sewing ring to the tissue surrounding the valvular orifice. The surgeon or an assistant typically holds the prosthesis in position during the suturing operation, by use of a holding device which engages the body of the valve.

Once the prosthetic heart valve is in place, it sometimes becomes necessary to rotate or reposition the valve. This is generally accomplished by reattaching the holder to the valve and rotating the holder.

Reusable holding devices, although extensively used for holding the heart valve during the suturing procedure, all suffer from several problems. Thus, they require a considerable amount of time for the surgeon both to premount the prosthesis on them, and, if necessary, reattach the holder during the surgical procedure. These holders generally comprise complex mechanisms in which an advancing screw thread causes two or more fingers to spread apart and engage a surface of the prosthetic heart valve. Numerous turns of the screw mechanism are usually required, depending upon the size of the valve being mounted on the holder. The surgeon is also required to position the holder on the heart valve in the proper orientation, whether it be aortic or mitral. If the holder is attached to the valve incorrectly or in the improper orientation, valuable time is lost which increases the risk to the patient.

Furthermore, the reusable heart valve holders have to be cleaned and sterilized after each operation, adding to the expense of a very expensive operation. Moreover, after many uses, there is a danger that the holder will malfunction, damage the valve, or even completely fail. A broken-off piece of the holder could cause severe injury to the patient or death. At best, a serious time delay will result with further danger to the patient.

Various types of disposable holders are currently available which, because they are prepositioned on the heart valve prior to surgery, overcome many of the disadvantages of the prior art reusable holders. However, no known prior art holder provides the ease of removal and reattachment coupled with the inexpensive manufacturability of valve holders constructed in accordance with this invention.

SUMMARY OF THE INVENTION

The prosthetic heart valve holder of the present invention overcomes the problems and disadvantages of the prior art by providing a disposable, single-piece holder having arms that are resiliently prepositioned on the valve body.

In addition, if reattachment is necessary in order to reorient the valve, this process is greatly facilitated by the ease with which the flexible, resilient arms of the holder are engaged on the valve. The holder has a narrow profile and is not an obstruction to the suturing process.

The present holder comprises a base or body portion having means for threadedly receiving a handle. Extending from and integral with the base are two flexible fingers which are biased in opposite directions when engaged within the interior portion of the annular valve ring. The resiliency of the fingers securely holds the heart valve ring in small retainers or detents provided near the distal ends of the fingers. In order to detach the holder from the valve, the surgeon simply manually depresses or squeezes the two fingers together slightly and removes the holder. Preferably, the holder is rotated about the shorter, more rigid finger. The longer, more flexible finger is provided with a tapered leading edge to facilitate reattachment. This longer finger is removed first during removal and is attached last during reattachment.

DETAILED DESCRIPTION OF THE INVENTION

Figure 1:
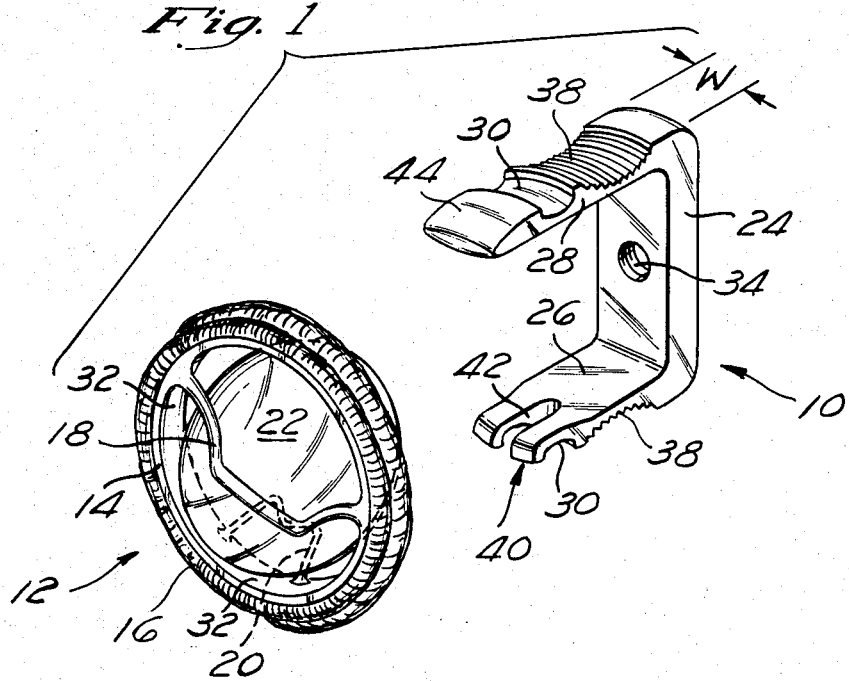
FIG. 1 is an exploded perspective view of the heart valve holder of the present invention and a typical prosthetic heart valve on which the holder may be prepositioned.

Although the heart valve holder 10 of the present invention comes preattached to a prosthetic heart valve 12, FIG. 1 illustrates these elements in exploded position for ease of illustration and description.

The prosthetic heart valve 12 shown in FIG. 1 is of a discoid or poppet type, although the present invention can be successfully utilized with any heart valve prosthesis. The discoid valve 12 shown comprises a main body portion or valve ring 14 which is surrounded by an annular suture ring 16 comprised, in this case, of a cloth material. The suture ring 16 is used for the actual attachment of the heart valve 12 to its orifice (not shown). The valve 12 also comprises a pair of opposite hinge members, 18 and 20, which have dual strut supports. The poppet disc 22, which is shown in the open position in FIG. 1, opens and closes in response to blood pressure using the hinge members 18 and 20 as camming surfaces. Discoid valves of similar construction are disclosed and claimed in U.S. Pat. Nos. 3,824,629 issued July 23, 1974, to Donald P. Shiley and 4,057,857 issued Nov. 15, 1977 to Bruce E. Fettel, both being assigned to Shiley, Inc., assignee of the present invention.

Figure 2:
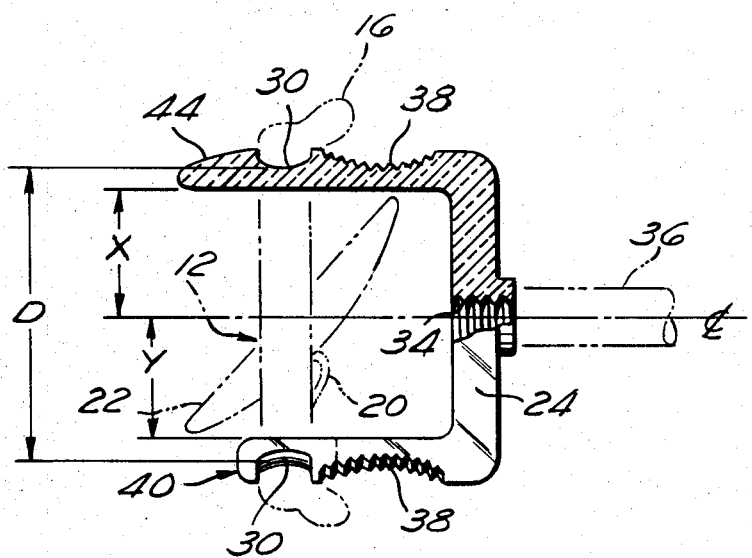
FIG. 2 is a partial cross-sectional side view of the holder of the present invention, illustrating an attached prosthetic heart valve in phantom.

The heart valve holder 10 of the present invention is illustrated in FIGS. 1 and 2. The holder 10 is a generally U-shaped device comprising a base portion or shoulder 24 with a pair of fingers 26 and 28 extending integrally and generally parallel from opposite ends of the shoulder 24. Located near the distal end of each finger 26 and 28 is a small detent 30 which engages the interior surface 32 of the annular valve ring 14 in order to hold it in position during suturing. The shoulder 24 is provided with a threaded hole 34 to receive a handle 36 for facilitating the holding of the valve 12 during suturing. The handle 36 is not shown in FIG. 1 and is shown partially in phantom in FIG. 2. Each finger 26 and 28 is also provided with a serrated, indented grip 38 which is located proximal of the detents 30 and provides a convenient location for the manual manipulation of the fingers 26 and 28 in order to remove the holder 10 from the valve 12 or reattach it, if necessary. The holder 10 can be constructed from any suitable material and in accordance with any suitable process, preferably by the injection-molding of a polypropylene acetal material.

The shorter finger 26 of the holder 10 has a forked end 40 which is inserted between the dual struts of the smaller hinge member 20. The central groove 42 forming the fork in the end 40 is for engagement with heart valves having single-strut hinge members (not shown) and is for use in connection with valves of that construction. Thus, regardless of the strut configuration of the valve, the forked-end finger 26 provides snug engagement with the valve ring in the event that rotation of the valve is necessary after implantation. The longer finger 28 advantageously is provided with a sloped and tapered leading edge 44 in order to facilitate reattachment as described in more detail below.

The heart valve holder 10 of the present invention is sized to fit the heart valve in order to provide a narrow profile such that the shoulder and legs do not extend beyond the outer diameter of the prosthetic valve, thus facilitating attachment of the valve in its orifice. Furthermore, the holder 10 itself is of a narrow width (indicated in FIG. 1 as the dimension W) so as to not significantly obstruct the suturing process and to avoid the entanglement of sutures. Advantageously the width W decreases as the size of the holder 10 decreases. Moreover, the holder 10 is preferably constructed from a clear polymer material so that it also does not create a visual obstruction to suturing. Preferably, the width W ranges from 0.300 in. to 0.460 in. depending on the size of the holder 10, while maintaining the desired degree of flexibility in the fingers 26 and 28.

In its relaxed state, shown in FIG. 1, the holder 10 is sized such that the distance D separating the detents 30 is greater than the inner diameter of the valve ring 14. In addition, the fingers 26 and 28 are sufficiently flexible so that when engaged with the valve ring 14, as shown in FIG. 2, the fingers 26 and 28 exert a resilient force and are biased in opposite directions against the valve ring 14 in order to hold it securely in the detents 30.

After the prosthetic valve has been sutured in place, the holder 10 is preferably removed by a rotational movement using the detent 30 of the smaller finger 26 as the axis of rotation. In other words, the longer finger 28 is depressed slightly at an approximate force of 1½ pounds so that it slips freely within the inner surface of the valve ring 14. The entire holder 10 is then rotated about the detent 30 of the small finger 26 so that the tapered end 44 of the larger finger 28 clears the valve ring 14. The shorter finger 26 can then be removed from the valve 12. Although removal and reattachment can also be accomplished by simultaneously depressing both fingers 26 and 28 slightly until they slip freely within the inner surface of the valve 12, the rotational removal movement described above avoids any serious trauma to the patient in whom the valve 12 has just been implanted. Reattachment of the holder 10, if necessary, in order to reposition the valve 12, is accomplished by a reverse process. The detent 30 of the smaller finger 26 is attached first to the valve 12 followed by the rotation of the holder 10 until the detent 30 of the longer finger 28 locks or snaps into place on the valve ring 14. Thus, the smaller finger 26 serves as a hinge or pivot for the snapping engagement of the longer finger 28 on the valve ring 14.

In order to facilitate removal and reattachment, the longer finger 28 is provided with a gently sloping, tapered leading edge 44. Thus, during removal, even if the force on the upper finger 28 is relaxed so that the tapered portion 44 engages the ring 14, it will still slip free of the ring 14 with very little friction. The tapered portion 44 is smooth and does not have any sharp or abrupt edges which could catch on the valve ring 14. Similarly, during reattachment, the tapered leading edge 44 of the longer finger 28 will permit it to slip into position within the valve ring 14 even if sufficient force has not been applied to depress the finger 28.

In order to facilitate removal and reattachment of the present holder in accordance with the rotational movement described above, the longer finger 28 is also advantageously constructed to be more flexible than the shorter finger 26 about which rotation is accomplished. Such enhanced flexibility is accomplished, in part, by the additional length of the longer finger 28 which makes it inherently more flexible. In addition, the distance X from the center line of the holder 10 to the longer finger 28 is slightly greater than the distance Y from the center line to the shorter finger 26, as illustrated in FIG. 2. This additional distance increases the flexibility of the longer finger 28. Of course, the amount by which the distance X exceeds the distance Y will depend upon the size of the valve for which the holder is constructed. However, generally X will exceed Y by a distance in the range of one to fifteen percent (1–15%) of the total distance (X plus Y) separating the two fingers 26 and 28. Moreover, increased flexibility is further achieved by a longer finger 28 which is slightly thinner than the shorter finger 26 in the plane shown in FIG. 2.

As described above, a significant advantage of the present invention is that the holder 10 comes preattached to the valve 12 in the correct position for implantation. In FIG. 2, the valve 12 is shown in phantom in the aortic position; however, the holder 10 of the present invention can advantageously also hold the valve 12 in the reverse or mitral position. Thus, there is no time wasted while the surgeon attaches the holder to the valve. Furthermore, the surgeon is not relieved upon to attach the holder in the correct position, either aortic or mitral. If reattachment becomes necessary, this is quickly and easily accomplished by the flexible finger construction of the present holder. Furthermore, the holder of the present invention is inexpensive to manufacture and is disposable, eliminating any risk of failure due to reuse.

We claim:

1. A device for facilitating the surgical replacement of a heart valve of a patient and for reducing the time required for said surgical replacement in order to decrease the danger to the life of said patient, comprising:
   a disposable holder adapted to be correctly prepositioned on said prosthetic heart valve for holding said prosthetic heart valve in place during replacement, said holder comprising:
   a body;
   means on said body and integral therewith, for flexibly releasably engaging said prosthetic heart valve, said integral engagement means providing the sole means for holding said valve in position during implantation; and means on said engagement means for manually manipulating said engagement means in order to remove said holder from said prosthetic heart valve following implantation.

2. The device of claim 1 wherein said manual manipulation means of said holder further comprises means for reattaching said holder to said prosthetic heart valve to reposition said valve, if necessary.

3. The device of claim 1 wherein said means on said body for flexibly, releasably engaging said prosthetic heart valve comprises a pair of flexible fingers integrally mounted at opposite ends of said body.

4. The device of claim 3 wherein one of said fingers provides an axis of rotation for facilitating removal of said disposable holder from said heart valve.

5. A disposable heart valve holder adapted to be mounted on a prosthetic heart valve for human implantation, comprising:

a shoulder; and plural fingers integrally mounted on said shoulder for resilient, releasable engagement with said valve such that said fingers are in a flexed state when engaged with said valve, said fingers including means for gripping said valve to substantially prevent movement of the holder in an axial direction relative to the valve.

6. The holder of claim 5 wherein said fingers are provided with serrations for manually manipulating said fingers to remove or reattach said holder to said prosthetic heart valve.

7. The holder of claim 5 wherein the width of said shoulder is less than the diameter of said valve in order to provide means for avoiding obstacles to the implantation of said valve.

8. The holder of claim 5 wherein said holder is comprised of a clear material in order to avoid visual obstacles to the implantation of said valve.

9. A heart valve holder adapted for use with an annular prosthetic heart valve having an interior surface, comprising:

at least one pair of arms for engagement with said valve, said arms being biased in opposite directions from one another and against said interior surface of said heart valve, to provide the sole means for holding said heart valve in position during replacement surgery, wherein each pair of arms has one arm which is relatively more flexible than the other.

10. The holder of claim 9 wherein said arms are inherently resilient to provide said holding means for said heart valve.

11. The holder of claim 9 wherein said arms, when not attached to said heart valve, are separated by a distance greater than the diameter of said interior surface in order to provide said holding means.

12. A holder prepositioned on a prosthetic heart valve adapted to be rotatably removed from said valve, said holder comprising:

pivot means releasably mounted on said heart valve for pivoting about the inner periphery of said heart valve; and locking means pivoted about said pivot means for releasable, flexible engagement of said heart valve, said locking means being relatively more flexible than said pivot means.

13. The holder of claim 12 wherein said locking means are manually snapped into position on said valve.

14. The holder of claim 13 wherein said locking means are provided with a tapered, leading edge to facilitate the snapping engagement of said locking means with said valve.

15. The holder of claim 12 wherein said heart valve is annular and has an interior surface, said pivot means and said locking means engaging said interior surface of said annular heart valve and being biased in opposite directions in order to mount said heart valve on said holder.

16. The holder of claim 12 wherein said locking means is longer than said pivot means in order to enhance its flexibility.

17. The holder of claim 12 wherein the distance from the center line of said holder to the locking means is greater than the distance from the center line of said holder to the pivot means, in order to increase the flexibility of the locking means.

18. The holder of claim 12 wherein the locking means is thinner than the pivot means when viewed in a vertical plane, in order to increase the flexibility of the locking means.

19. A method for removing a heart valve holder from a prosthetic heart valve to which said holder has been preattached, said holder comprising a pair of fingers in snapping engagement with said heart valve, comprising the steps of:

unsnapping a first finger from said heart valve;

rotating said holder about the inner periphery of said heart valve so that said first finger is detached from said heart valve; and removing a second finger from said heart valve, said second finger being relatively less flexible than said first finger.

20. A method for reattaching a holder to a prosthetic heart valve wherein the steps of claim 19 are reversed.

* * * * *